United States Patent [19]

Magnus

[11] Patent Number: 5,739,337
[45] Date of Patent: Apr. 14, 1998

[54] PROCESS FOR PREPARING DIBENZO-1-CARBOXAMIDO-1,4-AZABICYCLO[3.2.1]OCTANES

[75] Inventor: Philip D. Magnus, Austin, Tex.

[73] Assignee: Neurogen Corporation, Branford, Conn.

[21] Appl. No.: 613,030

[22] Filed: Mar. 8, 1996

[51] Int. Cl.$^6$ .................................................. C07D 221/22
[52] U.S. Cl. ........................... 546/72; 546/144; 564/221; 564/272; 564/374
[58] Field of Search .................................. 546/72, 144

[56] References Cited

U.S. PATENT DOCUMENTS

| | | | |
|---|---|---|---|
| 4,399,141 | 8/1983 | Anderson et al. | 546/72 |
| 4,477,668 | 10/1984 | Bender et al. | 546/72 |
| 5,196,415 | 3/1993 | Monn et al. | 546/72 |
| 5,512,575 | 4/1996 | Jacobs | 514/256 |

FOREIGN PATENT DOCUMENTS

| | | |
|---|---|---|
| 2 004 872 | 4/1979 | United Kingdom . |
| 2 061 947 | 5/1981 | United Kingdom . |

OTHER PUBLICATIONS

Rogawski, et al., (1991), "Anticonvulsant Activity of Low–Affinity Uncompetitive N–Methyl–D–aspartate Antagonist (±)–5–Aminocarbonyl–10,11–dihydro–5H–dibenzo[a,d]cyclohepten–5,10–imine(ADCI): Comparison with the Structural Analogs Dizocilpine (MK–801) and Carbamazepine," *J. Pharmacology and Experimental Therapeutics*, vol. 259, No. 1, pp. 30–37.

*Primary Examiner*—Donald G. Daus
*Attorney, Agent, or Firm*—McDonnell Boehnen Hulbert & Berghoff

[57] ABSTRACT

Disclosed are a process and novel compounds useful for preparing compounds of formula I

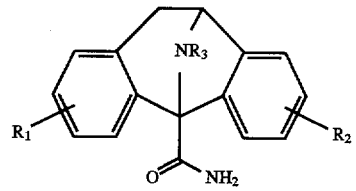

wherein
$R_1$ and $R_2$ independently represent hydrogen, inorganic or optionally substituted organic substituents; and
$R_3$ is hydrogen, or an optionally substituted organic group,
the process comprising cyclizing a tetrahydroisoquinoline of the formula

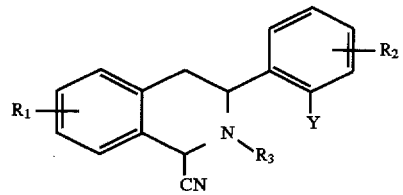

where Y is a leaving group, in the presence of a stong base.

The invention also encompasses a process for preparing the tetrahydroisoquinoline; and a process for converting the tetrahydroisoquinoline to the final amide I.

8 Claims, No Drawings

PROCESS FOR PREPARING DIBENZO-1-CARBOXAMIDO-1,4-AZABICYCLO[3.2.1] OCTANES

BACKGROUND OF THE INVENTION

1. Field of the Invention

This invention relates to the field of pharmaceutical chemistry, and provides an advantageous process for preparing dibenzo-1-carboxamido-1,4-azabicyclo[3.2.1] octanes.

2. Description of the Related Art

U.S. Pat. No. 5,196,415 discloses various dibenzo-1-carboxamido-1,4-azabicyclo[3.2.1]octanes (5-aminocarbonyl-5H-dibenzo[a,d]-cyclohepten-5,10-imines) and methods for preparing such compounds. The methods disclosed there involve conversion of C5-unsubstituted-10,11-dihydro-5H-dibenzo[a,d] cyclohepten-5,10-imines into their N-tert-butylformamidine derivatives followed by formation of the C5-substituted ethyl ester. After removal of the tert-butylformamidine moiety from the nitrogen atom of the ring system, the ester functionality is replaced with an amide group by warming the ester in methanol with the appropriate amine derivative. If N-substitution is desired, the secondary amine is allowed to react with the appropriate alkyl halide in the presence of a suitable base. This series of reactions produces a racemic mixture of dibenzo-1-carboxamido-1,4-azabicyclo[3.2.1] octanes, i.e., a racemic mixture of 5-aminocarbonyl-5H-dibenzo[a,d]cyclohepten-5,10-imines.

Racemic mixtures of 5-aminocarbonyl-5H-dibenzo[a,d] cyclohepten-5,10-imines are known to have pharmacological activity as anticonvulsant agents. See, for example, Rogawski et al., 1991, *J. Pharmacology and Experimental Therapeutics*, 259: 30–37, and Grant et al, 1992, *J. Pharmacology and Experimental Therapeutics*, 260: 1017–1022.

SUMMARY OF THE INVENTION

The present invention provides a novel method for preparing dibenzo-1-carboxamido-1,4-azabicyclo[3.2.1] octanes in good yield. This process involves an intramolecular cyclization of 3-(2-halophenyl)-1,2,3,4-tetrahydroisoquinolines using a strong base to yield a dibenzo-1-cyano-1,4-azabicyclo[3.2.1]octane. Subsequent reduction of the cyano group using conventional methods leads to the desired dibenzo-1-carboxamido-1,4-azabicyclo [3.2.1]octanes.

Thus, the invention provides a process for preparing a compound of formula I:

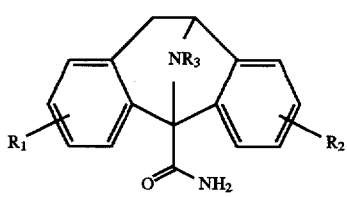

wherein $R_1$ and $R_2$ are independently selected from hydrogen, linear or branched alkyl groups of from one to about ten carbon atoms, alkenyl groups from two to about ten carbon atoms, alkynyl groups from two to about ten carbon atoms, hydroxyl, amino, alkylamino, alkoxy, cyano, nitro, haloalkyl, and mercapto, and $R_3$ is hydrogen, linear or branched alkyl having from one to about ten carbon atoms, alkenyl groups having from two to about ten carbon atoms, alkynyl groups having from two to about ten carbon atoms, hydroxyl, phenyl, haloalkyl, aminoalkyl, 1-phenylmethyl, 2-phenylmethyl, alkoxyalkyl, and hydroxyalkyl, any of the said groups being optionally substituted by alkyl, oxo, thio, alkoxy, hydroxy, amino, alkylamino, phenyl, haloalkyl and thio.

The process comprises cyclizing a compound of the formula II

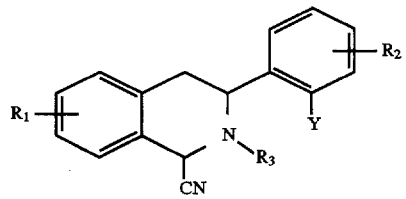

in the presence of a stong base,
where $R_1$, $R_2$, and $R_3$ are defined above, and Y is a leaving group capable of being displaced in an aromatic nucleophilic substitution reaction by a strong nucleophile.

The invention also provides methods for preparing compounds of formula II which process comprises treating a compound of formula III

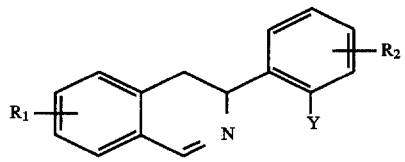

where the substituents are defined above, with a compound capable of providing the group $R_3$, and subsequently treating the product of that reaction with a cyano compound.

The invention further provides processes for preparing compounds of formula III, comprising preparing a formamide from a 1-amino-1,2-diphenyl ethane, and subsequently converting the formamide into a compound of formula III via an intramolecular Friedel-Crafts acylation using an iminoyl halide formed from the formamide.

The invention further encompasses the novel intermediates involved in the inventive process for preparing compounds of formula I. It also encompasses the methods for preparing those intermediates.

DETAILED DESCRIPTION OF THE INVENTION

In this document, all temperatures will be stated in degrees Celsius. All amounts, ratios, concentrations, proportions and the like will be stated in weight units, unless otherwise stated, except for ratios of solvents, which are in volume units.

Where the term 'alkyl' is used, either alone or within other terms such as 'haloalkyl' or 'alkylamino' the term 'alkyl' embraces linear or branched radicals having one to about ten carbon atoms. Preferred alkyl radicals are "lower alkyl" radicals having from one to about five carbon atoms. The term 'cycloalkyl' embraces radicals having from three to about ten carbon atoms, such as cyclopropyl and cyclobutyl. The term "haloalkyl" embraces radicals wherein one or more of the alkyl carbon atoms is substituted with one or more halogens atoms, preferably selected from fluoro, chloro and bromo. Specifically embraced by the term 'haloalkyl' are monohaloalkyl, dihaloalkyl and polyhaloalkyl groups. Examples of a polyhaloalkyl are trifluoromethyl, 2,2,2-trifluoroethyl and perfluoroethyl. The term 'alkenyl' embraces linear or branched radicals having from two to about ten carbon atoms and containing at least one double bond. The term 'alkynyl' embraces linear or branched radicals having from two to about ten carbon atoms containing at least one carbon-carbon triple bond. The term 'alkoxy' embraces linear or branched oxy-containing radicals having alkyl portions of from one to about ten carbon atoms, such as methoxy group. The alkoxy radicals may be further substituted with one or more halo atoms, such as fluoro, chloro or bromo to provide haloalkoxy groups. The term 'alkylamino' embraces linear or branched nitrogen containing radicals where the nitrogen atom may be substituted with from one to three alkyl radicals of from one to about ten carbon atoms, such as N-methylamino and N,N-dimethylamino.

Specific examples of alkyl groups are methyl, ethyl, propyl, isopropyl, n-butyl, isobutyl, tert-butyl, sec-butyl, neopentyl and n-pentyl. Typical alkenyl groups may have one unsaturated double bond, such as allyl or may have a plurality of double bonds.

By "racemic mixture" as used herein is meant a 50:50 by weight mixture of two enantiomers.

The following group of representative products of the process and of this invention will be mentioned, to assure that the reader fully understands the overall purpose of the process:

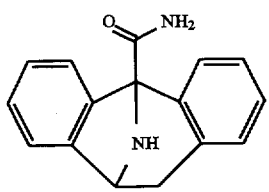

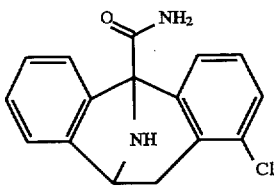

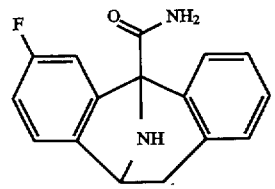

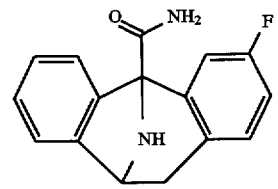

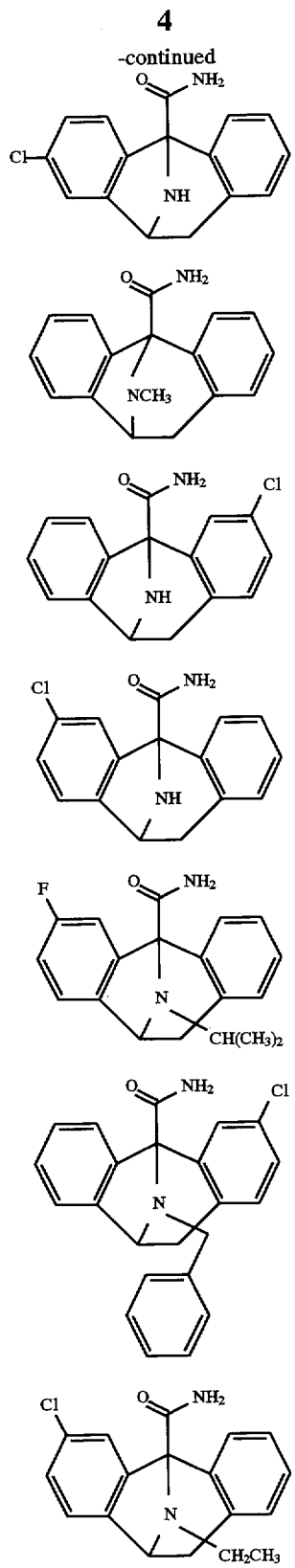

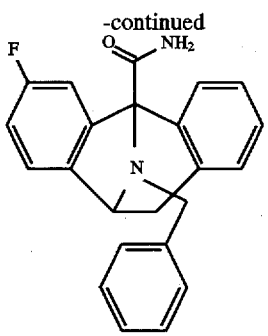

U.S. Pat. No. 5,196,415 indicates that the compounds preparable by the inventive methods are useful for treatment of patients with generalized epilepsy or partial (symptomatic) epilepsy. These compounds are also useful for treating drug craving in patients addicted to cocaine.

Administration of compounds within Formula I to humans can be by any technique capable of introducing the compounds into the bloodstream of a human patient, including oral administration, and by intraveneous, intramuscular and subcutaneous injections.

Compounds indicated by prophylactic therapy will preferably be administered in a daily dose generally in the range of 0.1 mg to 100 mg per kilogram of body weight per day. A more preferred dosage will be in the range of 1.0 to 50 mg per kilogram of body weight. A suitable dose can be administered in suitable sub-doses per day.

The active compound is usually administered in a pharmaceutically acceptable formulation, although in some acute-care situations a compound of Formula I may be administered alone. Such formulations may comprise the active compound with one or more pharmaceutically acceptable carriers or diluents. Other therapeutic agents may also be present in the formulation. A pharmaceutically acceptable carrier or diluent provides an appropriate vehicle for delivery of the active compound without undesirable side effects. Delivery of the active compound in such formulations may be by various routes such as oral, nasal, buccal or sublingual, or by parenteral administration such as subcutaneous, intramuscular, intravenous or intradermal routes. Delivery of the active compound may also be through the use of controlled release formulations in subcutaneous implants.

Formulations for oral administration may be in the form of capsules containing the active compound dispersed in a binder such as gelatin or hydroxypropylmethyl cellulose, together with one or more of a lubricant, preservative, surface acting or dispersing agent. Such capsules or tablets may contain controlled release formulation as may be provided in a disposition of active compound in hydroxypropylmethyl cellulose.

Formulations for parental administration may be in the form of aqueous or non-aqueous isotonic sterile injection solutions or suspensions. These solutions or suspensions may be prepared from sterile powders or granules having one or more of the carders or diluents mentioned for use in the formulations for oral administration.

The compounds of formula I are prepared according to the invention by cyclizing 3-(2-halophenyl)-1,2,3,4-tetrahydroisoquinolines (formula II) in a mixture of a strong base such as sodium or potassium amide to form a dibenzo-1-cyano-1,4-azabicyclo[3.2.1]octane. Conversion of the resulting cyano derivative to the desired dibenzo-1-carboxamido-1,4-azabicyclo[3.2.1]octane is achieved using conventional reduction methods.

As noted above, the 3-(2-halophenyl)-1,2,3,4-tetrahydroisoquinolines of formula II are prepared by treating a dihydroisoquinoline of formula III with a halide capable of providing the $R_3$ group, and subsequently treating the product of that reaction with a cyanide such as, for example, sodium or potassium cyanide.

Dihydroisoquinoline III may be prepared according to the reactions outlined in the following schemes.

SCHEME I

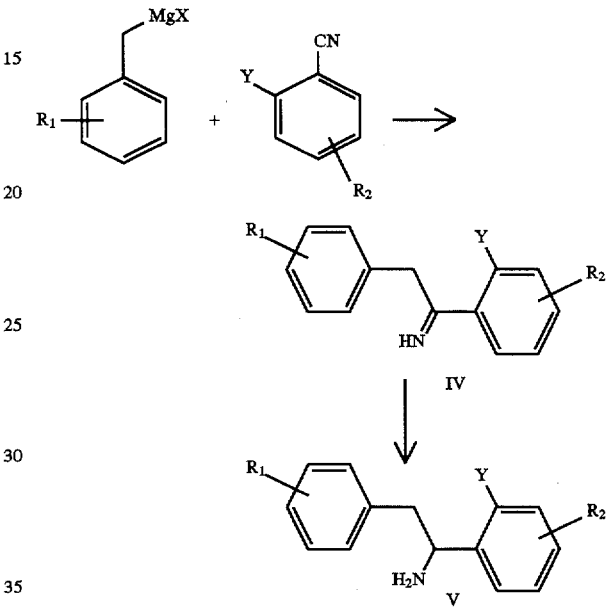

SCHEME II

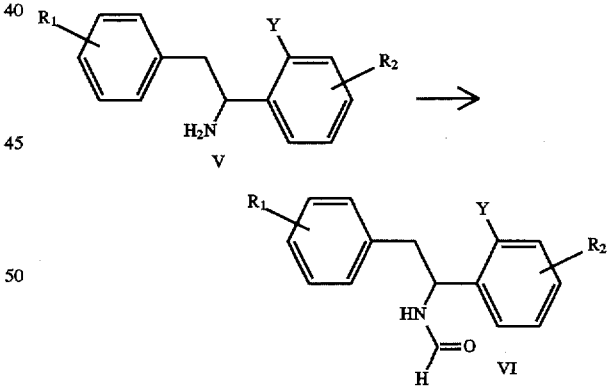

SCHEME III

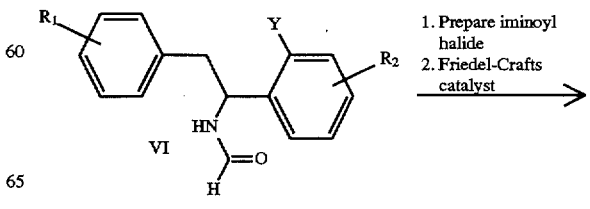

-continued
SCHEME III

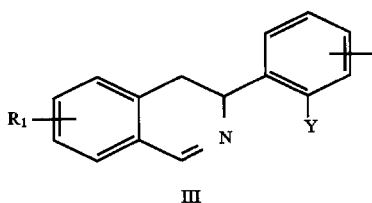

III

In Schemes I–III, $R_1$, $R_2$, and Y are defined as above for Formula I.

Preparation of Formamide VI

Amine V is prepared by reacting a suitably subsituted benzyl Grignard reagent in a conventional manner with a suitably substituted 2-halobenzonitrile in a suitable solvent. Representative solvents include diethyl ether and tetrahydrofuran. A slight excess of the Grignard reagent is preferably used to prepare imine IV. This reaction is conducted until the nitrile is consumed as shown by, for example, Thin Layer Chromatography (TLC), after which a reducing agent such as sodium borohydride is added to the mixture in a solvent such as methanol. The resulting mixture is then allowed to stir for at least about 8, and preferably for about 12–24, hours. Aqueous workup, extraction with a suitable solvent such as, for example, ethyl ether, gives amine V.

Conversion of amine V to formamide VI is accomplished by heating amine V in ethyl formate at reflux (about 55° C.) for about 1–5, and preferably about 2, hours. Formamide VI can be recrystallized from a suitable solvent. An example of a suitable solvent for recrystallization is 50:50 acetone/hexane (v/v).

Friedel-Crafts Cyclization

Formamide VI is cyclized to yield dihydroisoquinoline III by first converting the formamide to an iminoyl group This conversion may be accomplished by treating the formamide with a reagent such as, for example, oxalyl chloride, thionyl chloride, or phosphorous oxychloride at ambient temperature although temperatures of from about –25° to 50° C. may be employed. Typically the reagent is used in a slight excess compared to the starting formamide. The conversion of the formamide to iminoyl chloride is normally complete in less than one hour; however, depending on the substrate reactivity, reaction times of 15 minutes to 10 hours are suitable.

The formation of the iminoyl chloride is carried out in a solvent, and any inert solvent which is not significantly attacked by the conditions may be used. For example, halogenated solvents such as methylene chloride, 1,2-dichloroethane, chloroform, and the like may be used, as can aromatics such as petroleum ether, hexane, and the like, and nitrohydrocarbons such as nitrobenzene and nitroalkanes. A preferred solvent is methylene chloride.

Subsequent to formation of the iminoyl chloride, the reaction is cooled, typically to about –40° to 0° C., and preferably to about –10° C. Once the reaction mixture is cooled, a Friedel-Crafts catalyst is added and the resulting mixture is mixed for from about 1 to 24 hours. Preferably, the reaction is allowed to warm to ambient temperature, about 20° C., and then mixed for about 15 to 20, and more preferably 18, hours.

The acylation is a Friedel-Crafts acylation, and is carded out in the usual way. Either a Lewis acid or a proton acid may be used as the Friedel-Crafts catalyst; an excellent discussion of such catalysts appears in Olah, Friedel-Crafts and Related Reactions, Interscience Publ., New York, London and Sidney, 1963, Vol. I, Ch. III, and IV.

As explained by Olah, the classical Friedel-Crafts catalysts were Lewis acids. Such metal halides as aluminum chloride, aluminum bromide, and fluoride, boron trifluoride, boron trichloride, boron tribromide, titanium tetrachloride, titanium tetrabromide, stannnic chloride, stannic bromide, bismuth trichloride, and ferric chloride are well known catalysts and are useful in this acylation. The proton acid catalysts are also useful for this reaction, and include such substances as phosphoric acid, polyphosphoric acid, perchloric acid, chlorosulfonic acid, alkylsulfonic acids such as methanesulfonic and ethane sulfonic acids, toluenesulfonic and benzenesulfonic acids, sulfuric acid, chloroacetic acid, and trifluoroacetic acid. It is preferred to carry out the acylation with ferric chloride.

The acylation is carried out in a solvent, and any inert solvent which is not significantly attacked by the conditions may be used. For example, halogenated solvents such as methylene chloride, 1,2-dichloroethane, chloroform, and the like may be used, as can aromatics such as petroleum ether, hexane, and the like, and nitrohydrocarbons such as nitrobenzene and nitroalkanes. Preferrably, the acylation is conducted in the same solvent as the formation of the iminoyl chloride as described above.

The acylation portion of the conversion may be carried out at temperatures of from about ambient temperature to about 100° C., preferably at about the reflux temperature of the reaction mixture for processes catalyzed by proton acid catalysts, and preferably at about ambient temperature for Lewis acid catalyzed processes.

It is preferred to use a small molar excess of the Friedel-Crafts catalyst, i.e., from about 1.05 to 1.5, preferably 1.2, equivalents of the catalyst.

The dihydroisoquinoline III afforded by the acylation may be isolated from the reaction mixture by normal aqueous workup. No further purification of dihydroisoquinoline III is necessary pal or to its use in preparing the tetrahydroisoquinoline II.

Preparation of Tetrahydroisoquinoline

Dihydroisoquinoline III is converted to tetrahydroisoquinoline II by first treating a the dihydroisoquinoline with a reagent capable of providing the $R_3$ group. Where $R_3$ is other than hydrogen, the reagent may be a halo compounds, i.e., an organic halide. Where $R_3$ is hydrogen, the nitrogen is optionally protected with a suitable nitrogen protecting group. The protecting group is removed when convenient during the synthesis of the product of formula I. E.g., the protecting group may be removed subsequent to the preparation of the amide of formula I.

Suitable halides include such as various alkyl, alkenyl, alkynyl, or arylalkyl halides. Representative alkyl halides include, for example, methyl, ethyl, or propyl halides. Representative alkenyl halides include allyl halides, 4-halo-3-butenyl halides and the like. Representative alkynyl halides include propargyl halides and the like. Suitable arylhalides include benzyl, phenyethyl, or phenylpropyl halides. These reagents are optionally substituted with, for example, alkyl, oxo, thio, alkoxy, hydroxy, amino, alkylamino, phenyl, and thio groups.

Preferred halides are $C_1$–$C_3$ alkyl halides and benzyl halides. Preferred halogens forming the halide are bromide and chloride.

The halide may be reacted with the dihydroisoquinoline in the presence of an inert, polar solvent. An example of such a solvent is acetonitrile. Other suitable solvents will be apparent to those skilled in the art.

The dihydroisoquinoline is typically allowed to react with the halide for from about 1 to 24 hours. Normally, the endpoint of the reaction is determined when precipitation is complete. For example, the treatment of dihydroisoquinoline III where $R_1$ and $R_2$ are hydrogen and Y is chloro with benzyl bromide is complete within about 12 hours.

After treatment of the dihydroisoquinoline with the halide is complete, aqueous sodium or potassium cyanide is added to the mixture. The resulting mixture is allowed to mix for at least about 5 minutes and the tetrahydroisoquinoline II is isolated after standard aqueous workup.

Cyclization of Tetrahydroisoquinoline II

The cyclization of tetrahydroisoquinoline II to afford the 4-azabicyclo[3.2.1]octane is conducted in the presence of a strong base in an inert solvent such as for example, tetrahydrofuran (THF). The strong base is preferably formed prior to the addition of tetrahydroisoquinoline to the reaction mixture. Preferred bases include sodium and potassium amide. Other suitable bases include lithium diisopropylamide and sodium hydride.

In those cases where $R_3$ is hydrogen, the nitrogen atom bearing $R_3$ should first be protected by a suitable protecting group. Methods for protecting the nitrogen atom are known in the art.

The cyclization product may be isolated by an aqueous workup optionally followed by purification, for example by chromatography, to remove unreacted tetrahydroisoquinoline.

Reduction of the Cyano Group

The cyano substituent may be reduced to the amide functionality to afford 1-carboxamido-1,4-azabicyclo[3.2.1]octane I by any of a variety of methodologies known in the art.

Intermediates

As noted above, the invention further provides the novel intermediates utilized to prepare the compounds of formula I. Those intermediates include the following:

(A) an amine of formula VII

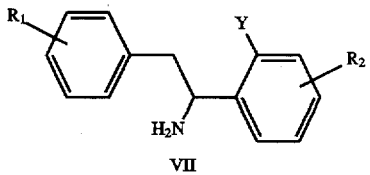

where
$R_1$ and $R_2$ are independently selected from hydrogen, linear or branched alkyl groups of from one to about ten carbon atoms, alkenyl groups from two to about ten carbon atoms, alkynyl groups from two to about ten carbon atoms, hydroxyl, amino, alkylamino, alkoxy, cyano, nitro, haloalkyl, and mercapto, and Y is a leaving group capable of being displaced in an aromatic nucleophilic substitution reaction by a strong nucleophile, and $R_2$ is defined above;

(B) an amide of formula VIII;

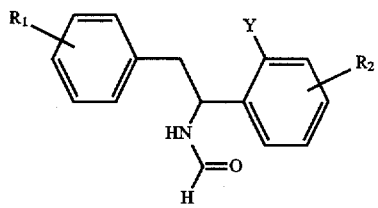

where $R_1$, $R_2$, and Y are defined above.

(C) a dihydroisoquinoline of formula IX

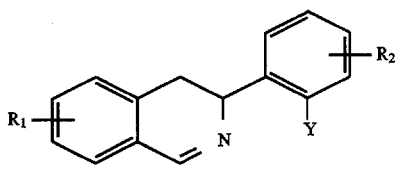

where $R_1$, $R_2$, and Y are defined above.

(D) a tetrahydroisoquinoline of formula X

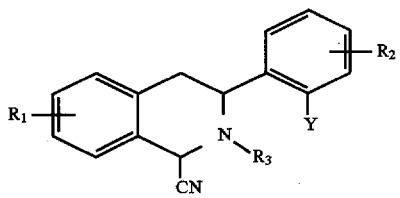

where $R_1$, $R_2$, and Y are defined above, and $R_3$ is hydrogen, linear or branched alkyl having from one to about ten carbon atoms, alkenyl groups having from two to about ten carbon atoms, alkynyl groups having from two to about ten carbon atoms, hydroxyl, phenyl, haloalkyl, aminoalkyl, 1-phenylmethyl, 2-phenylmethyl, alkoxyalkyl, and hydroxyalkyl, any of the said groups being optionally substituted by alkyl, oxo, thio, alkoxy, hydroxy, amino, alkylamino, phenyl, haloalkyl and thio.

(E) an imine of formula XI

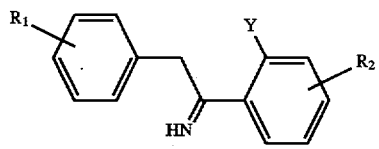

where $R_1$, $R_2$, and Y are defined above.

(F) an amine of formula XII

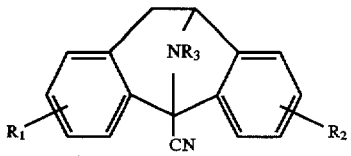

where $R_1$, $R_2$, and $R_3$ are defined above.

The disclosures in this application of all articles and references, including patents, are incorporated herein by reference.

The invention is illustrated further by the following examples which are not to be construed as limiting the invention in scope or spirit to the specific procedures and compounds described in them.

EXAMPLE 1

Part A

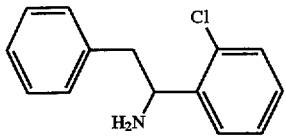

1

To benzyl magnesium chloride (1.0M in Et$_2$O, 1.03 eq.) is added 2-chlorobenzonitrile, and the reaction allowed to stir until complete as determined by TLC. NaBH$_4$ (11.0 g) and methanol (200 mL) are then added to the mixture and stirring is continued for an additional 16 hours (overnight). Aqeous workup, followed by removal of the solvent under reduced pressure afforded 23 g (35% yield) of 1.

Part B

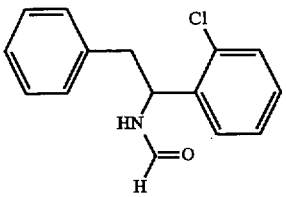

2

The entire product of part A of this example (23 g) is added to 200 mL of ethyl formate and the resulting mixture is heated at reflux for 2 hours. Removal of the solvent under reduced pressure affords 23 g of crude residue. The crude residue is recrystallized from 50:50 (v/v) hexane/acetone to yield a first crop of 14.5 g of crystalline 2.

Part C

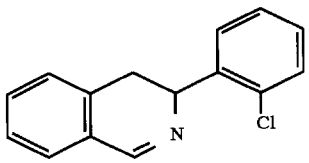

3

To formamide 2 (14.5 g) prepared in part B of this example in 500 mL of methylene chloride, is added 5.4 mL of oxalylchloride (1.1 eq.). The reaction is allowed to stir for about 30 minutes and then is cooled to about −10° C. To the cooled mixture is added 1.2 eq. of FeCl$_3$ and the resulting mixture allowed to stir at room temperature for about 18 hours. Aqueous workup yields 14 g of dihydroisoquinoline 3.

Part D

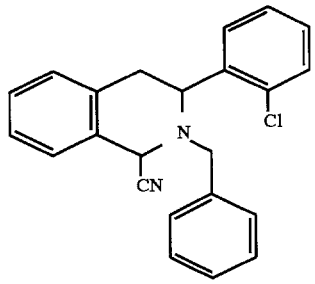

4

To a solution of dihydroisoquinoline 3 (1.18 g) in 25 mL of acetonitrile is added 0.7 mL of benzyl bromide (1.2 eq.). After precipitation is complete (about 12 hours), an aqueous solution of sodium cyanide is added. After stirring the mixture until shown to be complete by TLC, aqueous workup affords 1.15 g of tetrahydroisoquinoline 4.

Part E

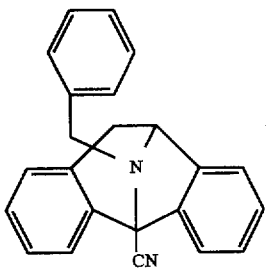

5

A solution of potassium amide in ammonia and THF is prepared and to that solution is slowly added dropwise a solution of tetrahydroisoquinoline 4 in THF. Aqueous workup and removal of solvent under reduced pressure afforded Dibenzo-1-carboxamido-1,4-azabicyclo[3.2.1] octane 5. Chromatography may be used to purify the product is desired.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude the specification.

What is claimed is:

1. A process for preparing a compound of the formula

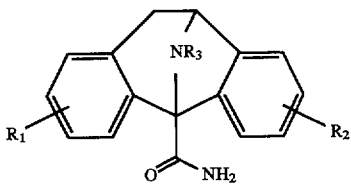

wherein

R$_1$ and R$_2$ are independently hydrogen or halogen;

R$_3$ is hydrogen, methyl, benzyl, or methoxymethyl;

the process comprising cyclizing a tetrahydroisoquinoline of the formula

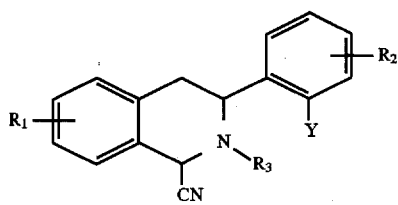

where Y is a leaving group,
in the presence of a strong base selected from alkali metal amides, lithium diisopropylamide and sodium hydride.

2. A process according to claim 1, wherein Y is chloro.

3. A process according to claim 1, wherein the tetrahydroisoquinoline is prepared by contacting a compound of the formula

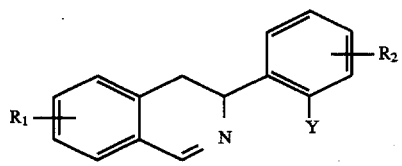

where $R_1$, $R_2$, and Y are defined above,
with a compound $R_3Z$, where $R_3$ is defined above and Z is a halide, to form a reaction mixture.

4. A process according to claim 3 wherein a cyanide compound is added to the reaction mixture.

5. A process according to claim 4, wherein the cyanide compound is sodium cyanide or potassium cyanide.

6. A process according to claim 3, wherein $R_3$ is $C_1$–$C_6$ alkyl, or arylalkyl where the alkyl portion is $C_1$–$C_6$ alkyl.

7. A process according to claim 3, wherein $R_3Z$ is methyl bromide, or benzyl bromide.

8. A process for preparing a compound of the formula:

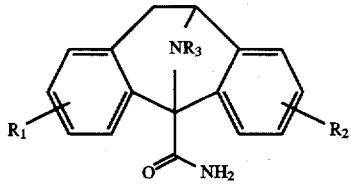

wherein
$R_1$ and $R_2$ are independently hydrogen or halogen;
$R_3$ is hydrogen, methyl, benzyl, or methoxymethyl;
the process comprising
(a) preparing an amine of the formula

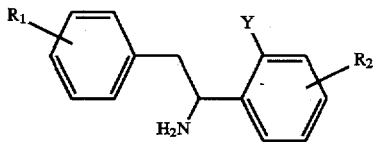

where and Y is a leaving group capable of being displaced in an aromatic nucleophilic substitution reaction by a strong nucleophile;

by reacting a Grignard reagent of the formula

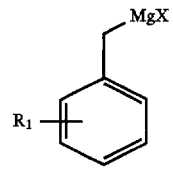

where X is a halogen and $R_1$ is defined above, with a 2-halobenzonitrile of the formula

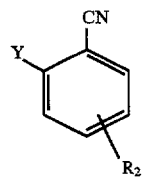

(b) converting the amine to an amide;

(c) preparing an iminoyl chloride from the amide;

(d) treating the iminoyl chloride with a Friedel-Crafts catalyst to provide a dihydroisoquinoline of the formula

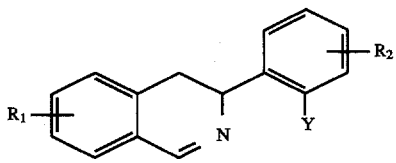

and (e) reacting the dihydroisoquinoline with a compound $R_3Z$ where $R_3$ is defined above and Z is a halide to form a reaction mixture and adding a cyanide compound to the mixture to yield a tetrahydroisoquinoline of the formula

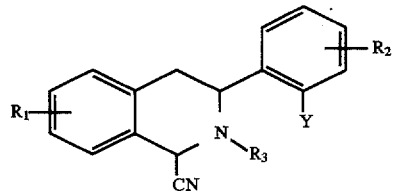

where $R_1$, $R_2$, $R_3$, and Y are defined above; and (f) cyclizing the tetrahydroisoquinoline in the presence of a base selected from alkali metal amides, lithium diisopropylamide and sodium hydride.

* * * * *